United States Patent
Hall et al.

(10) Patent No.: US 9,618,393 B2
(45) Date of Patent: Apr. 11, 2017

(54) APPARATUS FOR MEASURING HEXAVALENT CHROMIUM IN WATER

(71) Applicant: Freestone Environmental Services, Inc., Richland, WA (US)

(72) Inventors: Stephen H Hall, Pasco, WA (US); Kimberly Anne Schuyler, Kennewick, WA (US)

(73) Assignee: Freestone Environmental Services, Inc., Richland, WA (US)

(*) Notice: Subject to any disclaimer, the term of this patent is extended or adjusted under 35 U.S.C. 154(b) by 0 days.

(21) Appl. No.: 14/495,801

(22) Filed: Sep. 24, 2014

(65) Prior Publication Data
US 2016/0084759 A1    Mar. 24, 2016

(51) Int. Cl.
| | |
|---|---|
| *G01N 21/00* | (2006.01) |
| *G01J 3/50* | (2006.01) |
| *G01N 21/03* | (2006.01) |
| *G01N 33/18* | (2006.01) |
| *G01N 21/53* | (2006.01) |
| *G01N 21/51* | (2006.01) |

(52) U.S. Cl.
CPC .......... *G01J 3/501* (2013.01); *G01N 21/031* (2013.01); *G01N 21/0303* (2013.01); *G01N 21/532* (2013.01); *G01N 33/18* (2013.01); *G01N 2021/513* (2013.01)

(58) Field of Classification Search
CPC  G01J 1/1626; G01J 3/10; G01J 3/501; G01N 21/51; G01N 21/532; G01N 21/251

USPC .......... 356/432–440, 51, 402, 338, 409; 250/373, 372, 336.1
See application file for complete search history.

(56) References Cited

U.S. PATENT DOCUMENTS

| | | | | |
|---|---|---|---|---|
| 4,222,670 | A * | 9/1980 | Koshiishi | G01N 21/03 |
| | | | | 204/409 |
| 4,758,085 | A | 7/1988 | Lequime et al. | |
| 4,995,727 | A | 2/1991 | Kawagoe et al. | |
| 5,402,241 | A * | 3/1995 | Jeannotte | G01N 21/83 |
| | | | | 250/576 |
| 5,599,503 | A * | 2/1997 | Manz | B01L 3/502715 |
| | | | | 204/452 |
| 5,644,402 | A * | 7/1997 | Chevallet | A61M 1/1692 |
| | | | | 250/559.4 |
| 6,654,119 | B1 | 11/2003 | Gould et al. | |
| 6,809,810 | B2 * | 10/2004 | Carrillo | B01L 3/502715 |
| | | | | 356/246 |
| 7,491,366 | B2 * | 2/2009 | Tokhtuev | G01N 21/251 |
| | | | | 422/82.05 |
| 7,586,612 | B2 * | 9/2009 | Savatic | B01L 3/502715 |
| | | | | 356/436 |

(Continued)

*Primary Examiner* — Hoa Pham
(74) *Attorney, Agent, or Firm* — Seed IP Law Group LLP

(57) ABSTRACT

The present invention comprises an optical train (50) and optional wavelength-selective photodetectors. The optical train (50) uses reflecting elements (600) including mirrors and/or prisms to fold the light path of the transmitted UV light beam to direct it through the body (100) of the instrument, through a sample vessel (200) using at least one pass but preferably two or more passes and into illumination contact with a photodetector (400). With each additional pass, the Beer-Lambert path length is effectively increased. Separate second optical train (53) and third optical train (54) exist for the detection and measurement of scattered light by illumination contact with one or more photodetectors.

9 Claims, 11 Drawing Sheets

(56) References Cited

U.S. PATENT DOCUMENTS

| | | | | |
|---|---|---|---|---|
| 7,675,616 B1* | 3/2010 | Carney | ................... | G01J 3/02 356/326 |
| 2010/0302546 A1* | 12/2010 | Azimi | ................... | G01J 3/02 356/437 |
| 2011/0242523 A1* | 10/2011 | Hall | ................... | G01N 21/532 356/51 |
| 2012/0212739 A1 | 8/2012 | Aldstadt, III et al. | | |

* cited by examiner

US 9,618,393 B2

APPARATUS FOR MEASURING HEXAVALENT CHROMIUM IN WATER

FIELD OF THE INVENTION

This invention relates in general to chemical measurements and more particularly the quantity of a chemical in a solution and in particular to the use of colorimetric instruments for measuring the concentration of hexavalent chromium in water.

BACKGROUND OF THE INVENTION

An earlier U.S. Pat. No. 8,699,025 to Hall, herein noted as the parent invention, claims an apparatus and method for measuring hexavalent chromium in water based on colorimetric measurement of the chromate ion.

The present invention is an improvement upon the parent invention. This disclosure demonstrates the ability to significantly reduce the size of the colorimetric apparatus while also increasing analytical sensitivity.

SUMMARY OF THE INVENTION

The present invention comprises an optical train (50) and optional wavelength-selective photodetectors. The optical train (50) uses reflecting elements (600) including mirrors and/or prisms to fold the light path of the transmitted UV light beam to direct it through the body (100) of the instrument, through a sample vessel (200) using at least one pass but preferably two or more passes and into illumination contact with a photodetector (400). With each additional pass, the Beer-Lambert path length is effectively increased. Separate second optical train (53) and third optical train (54) exist for the detection and measurement of scattered light by illumination contact with one or more photo detectors.

DETAILED DESCRIPTION OF THE INVENTION

Figure 1:
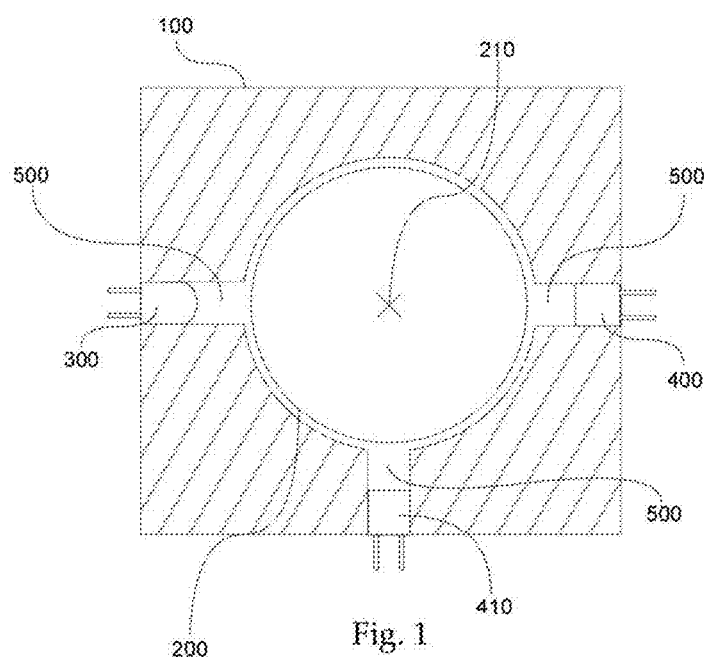
FIG. 1 illustrates the earlier instrument of U.S. Pat. No. 8,699,025 to Hall showing a sensor body (100), a sample vessel (200), a light source (300), a first photodetector (400), a second photodetector (410), a first light tunnel segment (500), a second light tunnel segment (500), and a third light tunnel segment (500). Seen is a first light tunnel segment (500) and a second light tunnel segment (500) are collinear forming a straight path from light source (300) to photodetector (400); and the said light path from light source (300) to photodetector (400) is mutually orthogonal with third light tunnel segment (500) and sample chamber axis (210).

The configuration of the invention disclosed provides for two or more passes of light through a turbid sample and for simultaneous measurement of light absorption and light scatter. Those of ordinary skill in optics will recognize that this structure can, in light of the main principle of the Beer-Lambert law, increase the analytical sensitivity of a colorimetric instrument in that this sensitivity is directly proportional to the path length of the analytical light beam as it passes through a sample. Disclosed and claimed herein is the structure causing the analytical light beam to make multiple passes through the sample. Second, the near-UV wavelengths used for chromate measurement can cause materials such as certain dyes and minerals to fluoresce. The emitted fluorescent light is necessarily of longer wavelength than the near-UV light source, and is visible to the human eye. If such dyes are dissolved in a sample, or if such mineral particles are suspended in a sample as turbidity, the emitted fluorescence is an additional source of light that may become an analytical interference if it reaches the photodetectors and adds to the measured light intensities. The silicon phototransistors used in the parent patent are sensitive to visible and infrared light as well as to UV light, so sample fluorescence is an analytical interference Photodetectors such as the indium-gallium-nitride (InGaN) photodiodes are sensitive to the near-UV analytical wavelength, but are blind to visible light, i.e., light having a wavelength greater than approximately 400 nm. Using such photodiodes, instead of silicon phototransistors, light intensity measurements will be unaffected by fluorescence.

Having UV light transmitted through the sample at least twice and detecting scattered light at more than one point along the transmitted light path increases signal-to-noise ratio, thus improving accuracy and sensitivity.

Finally, precision in the measured intensity of the scattered light is very important. Although the intensity of the scattered light is often extremely small compared to the intensity of the transmitted analytical beam, its effect on analytical accuracy can be significant.

The present invention uses a transparent cylindrical sample vessel (200) fitted into a sample chamber (110) within a supporting colorimeter body (100); the colorimeter body (100) is, in the preferred embodiment, formed of a non-reflective material such as black Delrin® polymer. Those of ordinary skills in these arts will recognize that other materials will also be available for the colorimeter body (100). The transmitted UV light beam is constrained and partially collimated by using an optical train (50) comprising at least one light source (300) emitting a light beam into the at least one optical train (50); the said light beam is directed by mirrors and/or prisms, identified here as reflective elements (600), through at least one light tunnel segment (500) formed into the body (100), reflected at each turn by a reflective element (600) and into illumination contact with at least one photodetector (400).

In the preferred embodiment the sample vessel (200) is cylindrical which, when filled with sample, acts as a lens to concentrate the light beam emitted from the light source (300) as it passes through the sample vessel (200), thus minimizing beam spread and loss of signal strength.

Figure 2:
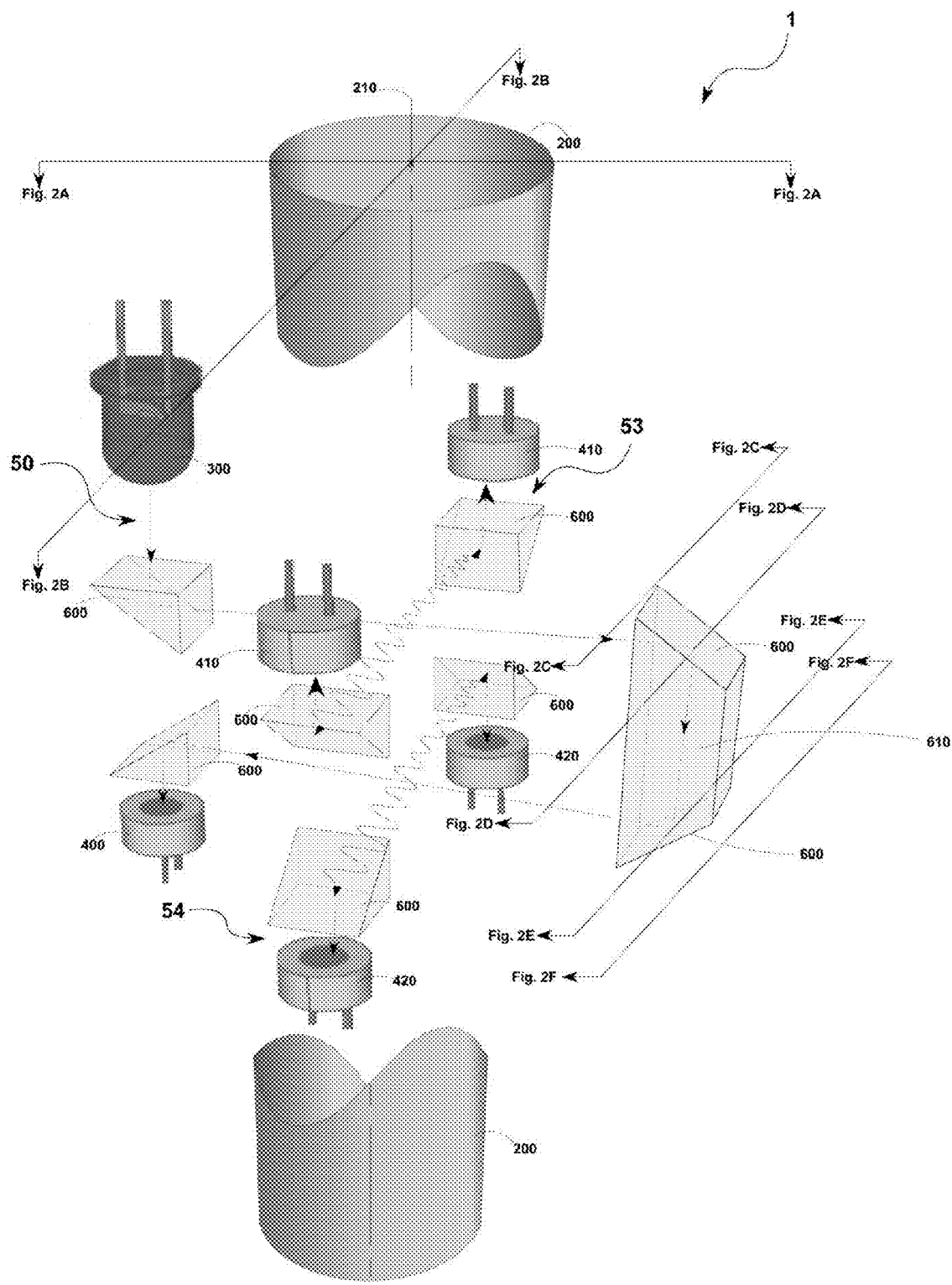
FIG. 2, FIG. 2a and FIG. 2b illustrates the colorimeter (1) of the present disclosure having a colorimeter body (100), sample chamber (110), outside (140), top (180), bottom (190), sample vessel (200), sample chamber axis (210) and a light source (300). Seen is a first photodetector (400), two second photodetectors (410) and two third photodetectors (420). Also seen an at least one optical train (50) and at least one light tunnel segment (500). Also seen are reflective elements (600) and reflective element spaces (700). Also seen is at least one dove prism (610) comprising two reflective elements (600).
Figure 2B:
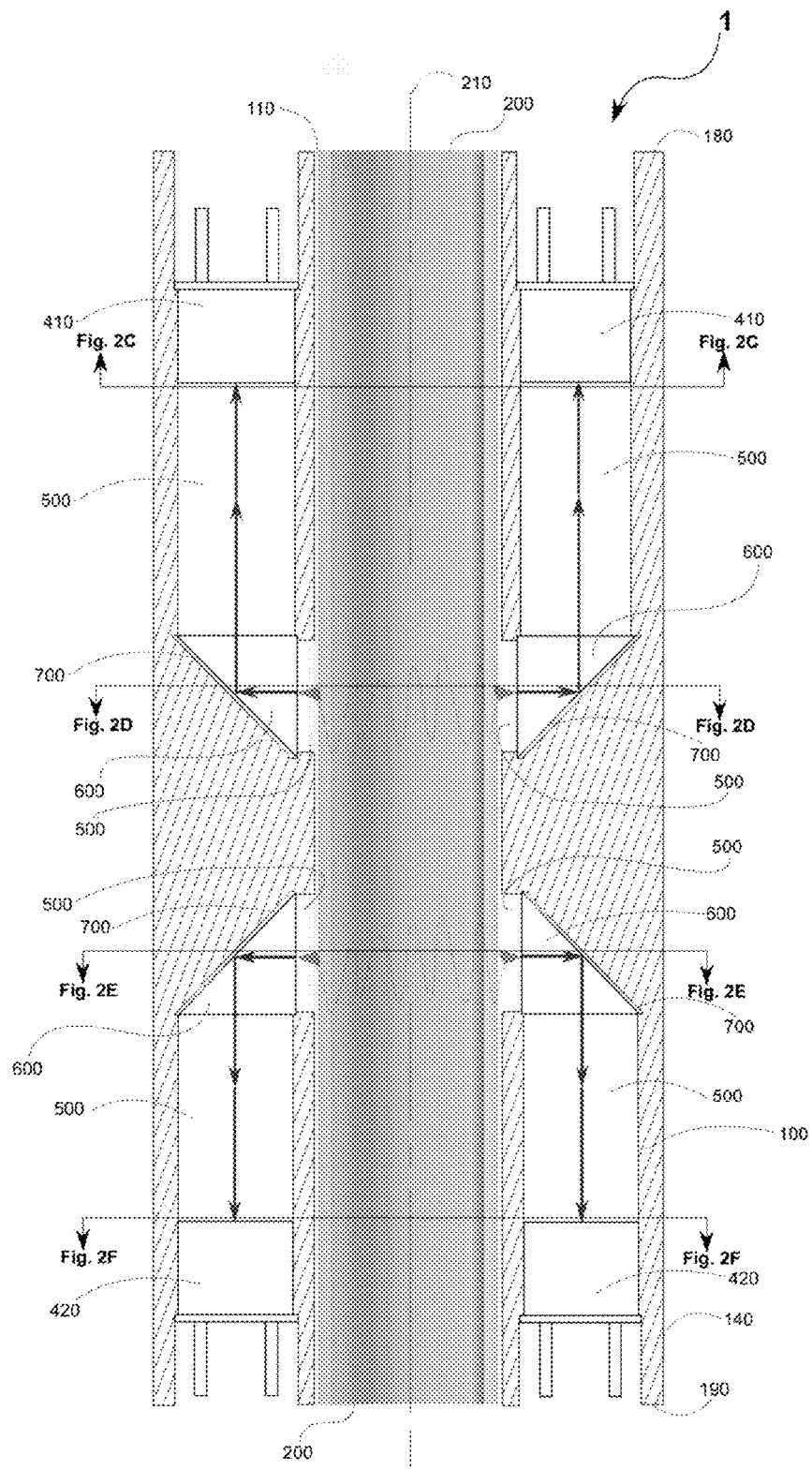
Figure 2A:
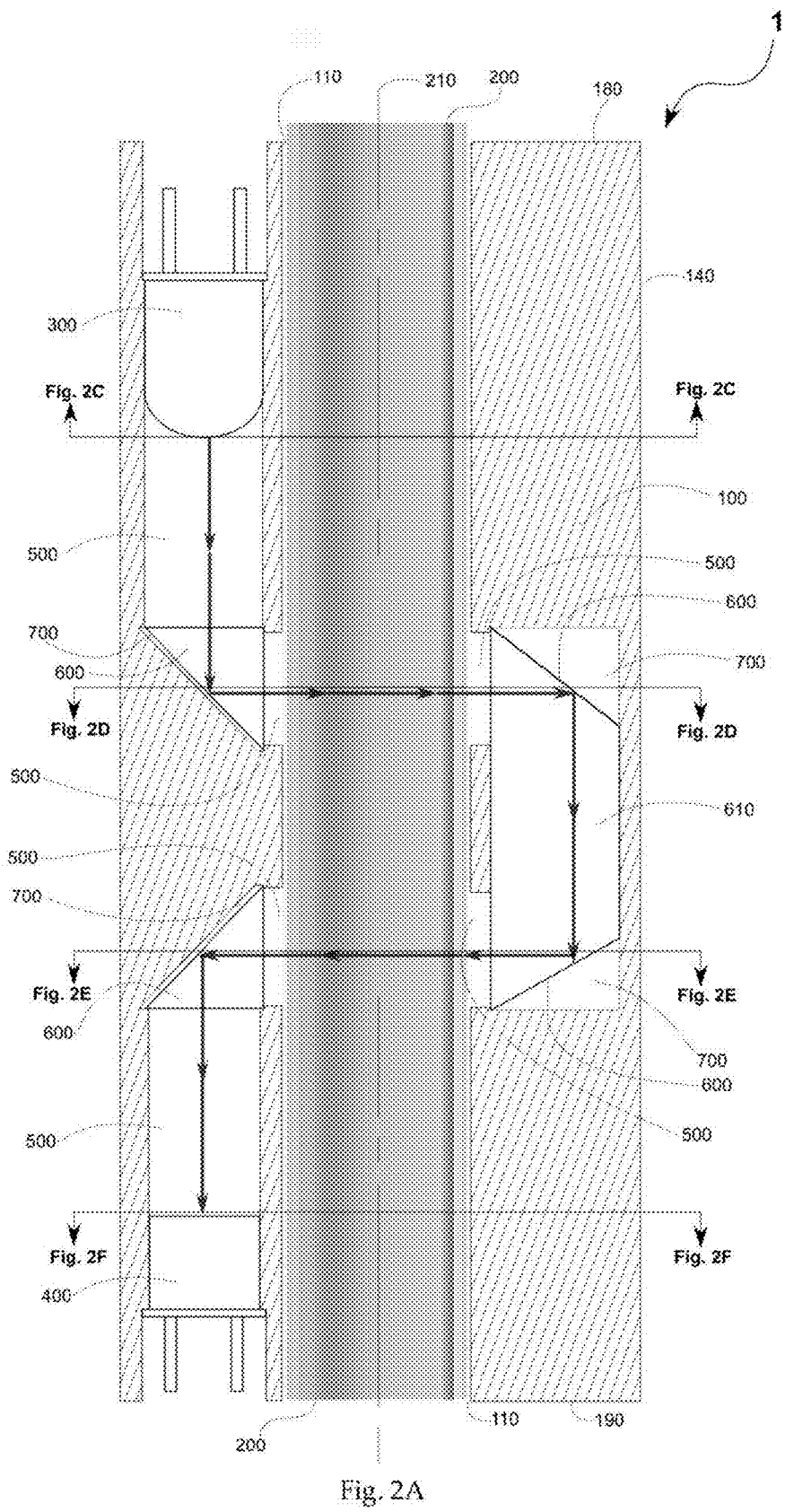
Figure 2C:
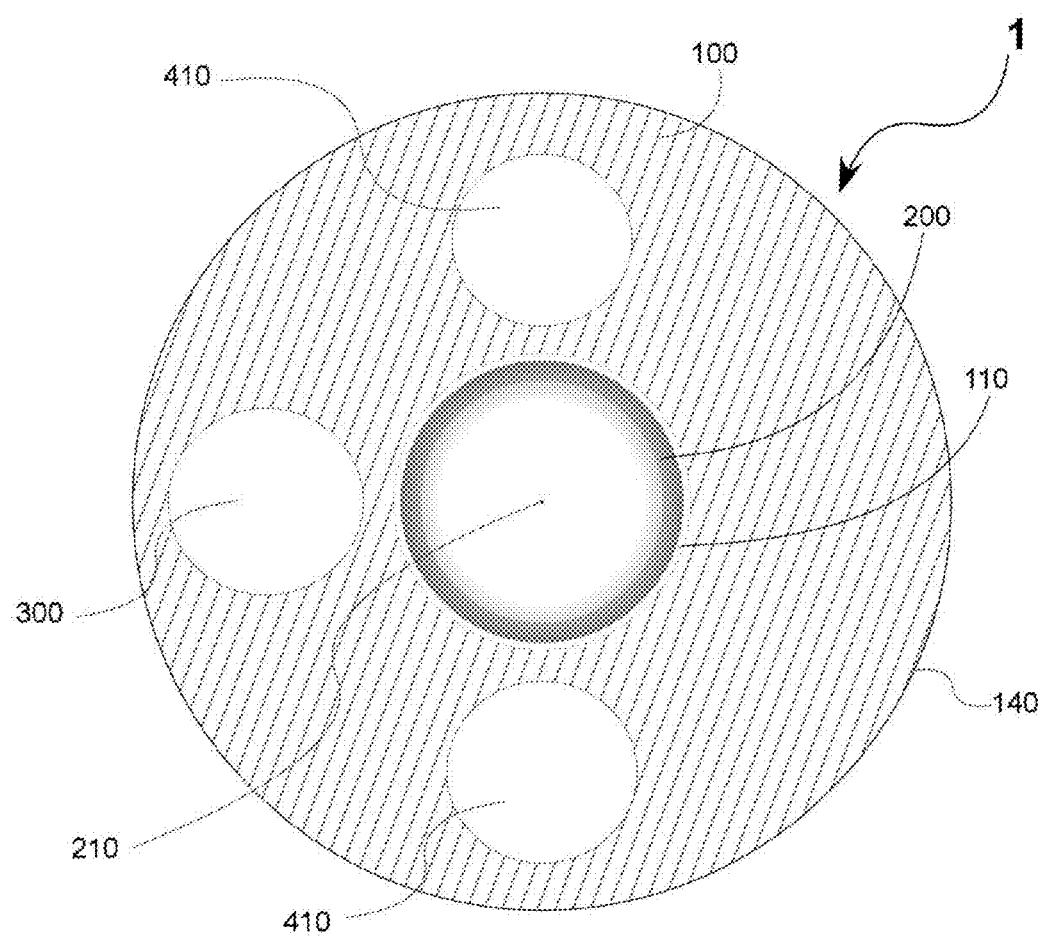
FIG. 2c illustrates cross section 2c from FIG. 2 showing the colorimeter (1), colorimeter body (100), sample chamber (110), sample chamber axis (210), outside (140), sample vessel (200), sample chamber axis (210), one light source (300). Seen is at least one second photodetector (410).
Figure 2D:
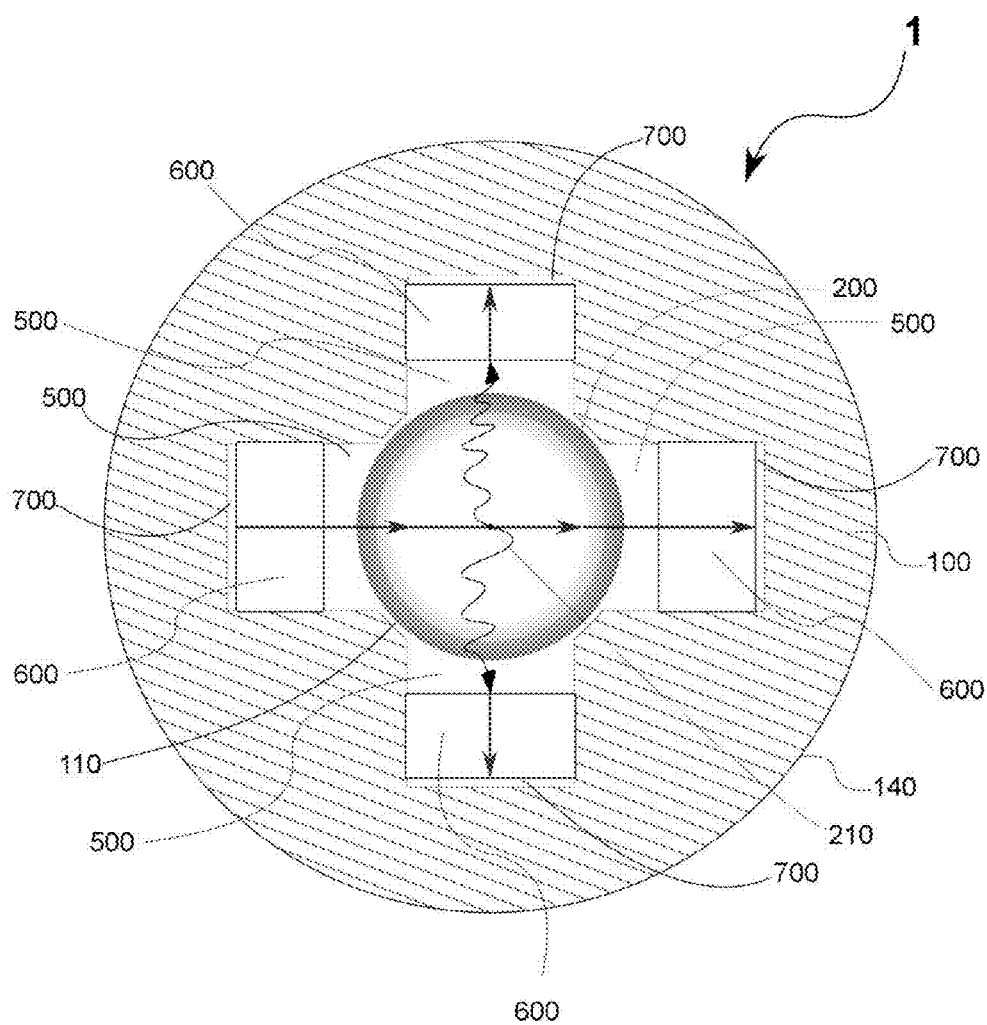
FIG. 2d shows section 2d from FIG. 2 illustrating colorimeter (1), colorimeter body (100), sample chamber (110), sample chamber axis (210), outside (140), sample vessel (200), sample chamber axis (210), light tunnel increments (500), reflective elements (600) and reflective element spaces (700).
Figure 2E:
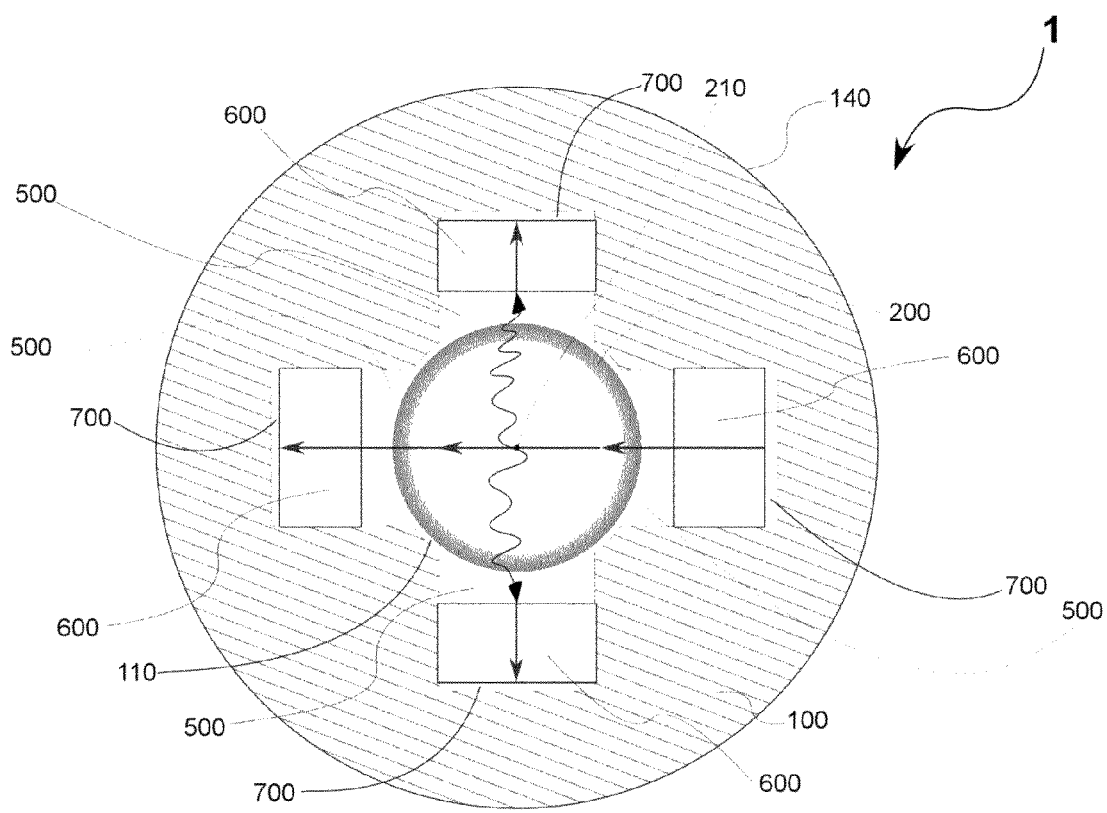
FIG. 2e shows section 2e from FIG. 2 illustrating colorimeter (1), colorimeter body (100), sample chamber (110), sample chamber axis (210), outside (140), sample vessel (200), sample chamber axis (210), reflective element (600) and reflective element spaces (700).
Figure 2F:
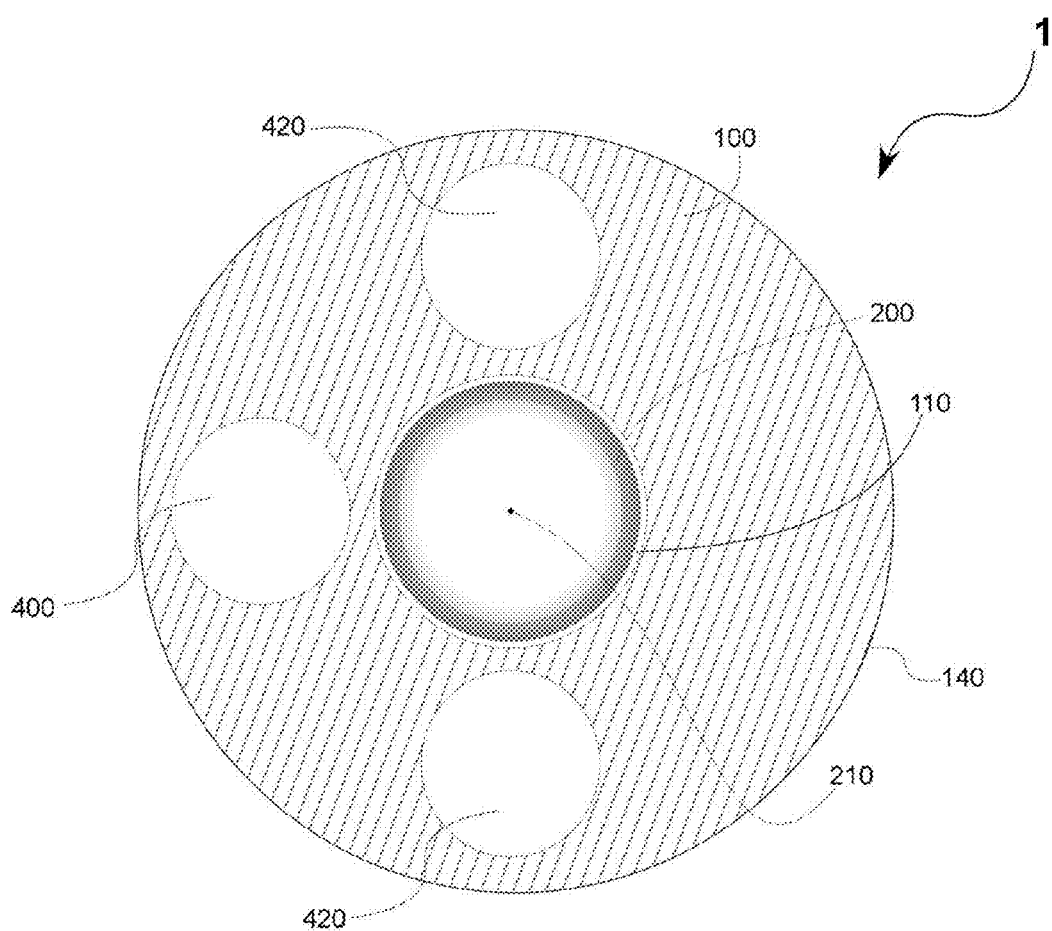
FIG. 2f is section 2f from FIG. 2 showing colorimeter (1), colorimeter body (100), sample chamber (110), sample chamber axis (210), outside (140), sample vessel (200), sample chamber axis (210), a first photodetector (400) and at least one third photodetector (420).

FIG. 2, FIG. 2a and FIG. 2b illustrate the preferred embodiment of the invention of this disclosure. Seen is a colorimeter (1) having a colorimeter body (100), the body (100) having a sample chamber (110); a sample vessel (200) is accommodated by the sample chamber (110); a sample is contained within the sample vessel (200). At least one light source (300) is affixed to the body (100); an incident beam, from the said at least one light source (300) is directed into an optical train (50) having at least one reflective element (600) directing the incident beam through the sample vessel (200) and sample, at least once, and into illumination contact with at least one photodetector (400); and, the said at least one photodetector (400) is affixed to the body (100) and is aligned, through the said optical train (50) and is distal to the light source (300); and, an output voltage from the said at least one photodetector (400) is a factor for determining the concentration of hexavalent chromium in the sample; and, at least one second optical train (53) having at least one reflective element (600) directing the said scattered light emanating from the sample vessel (200) and sample, at least once, and into scattered light illumination contact with at least one second photodetector (410); and, the said at least one second photodetector (410) is affixed to the body (100) and is aligned with the said second optical train (53) and produces an output voltage which is a factor for determining the concentration of hexavalent chromium in the sample.

Additional description of the preferred embodiment from FIG. 2, FIG. 2a and FIG. 2b is realized by the disclosure. Seen is a colorimeter (1) having a colorimeter body (100), the body (100) having a sample chamber (110); a sample vessel (200) is accommodated by the sample chamber (110); a sample is contained within the sample vessel (200). At least one light source (300) is affixed to the body (100); an incident beam, from the said at least one light source (300) is directed into an optical train (50), here utilizing a hole having reflective elements (600) directing the incident beam through the sample vessel (200) and sample, at least once, and into illumination contact with at least one photodetector (400); and, the said at least one photodetector (400) is affixed to the body (100), is aligned, through the said optical train (50), is distal from the at least one light source (300) and produces an output voltage which is a factor in determining the concentration of hexavalent chromium in the sample. The indicated optical train (50) utilizes at least one reflective element (600). Those of ordinary skill in the optical and instrument arts will recognize that such an optical train (50) may turn or redirect light, whether from a light beam or scattered light, several times thus necessitating multiple bends or folds which are facilitated by mirrors and prisms.

FIGS. 2, 2a and 2b also illustrate the optical train (50) forming a hole with bends, folds and turns using reflective elements (600) which, in this application are preferably prisms or mirrors used to re-direct transmitted and scattered light paths through the sample vessel (200). Persons of ordinary skill in the art of optics and instruments will recognize from FIG. 2 how the prisms or other reflective elements must be aligned and fixed to direct the transmitted and scattered light beams as shown in the figure. Persons so skilled will also recognize that if prisms are used as the reflective elements, clearance between the rear of the angled reflecting facet and the sensor body must be maintained to prevent optical contact between the facet and the sensor body and consequent light loss. In a preferred embodiment, a minimum of 0.25 mm clearance is used and is seen as reflective element space (700). The second photodetectors (410) and third photodetectors (420) occupy the four positions representing termini of scattered light beams paths in the at least one second optical train (053) and the at least one third optical train (54). Those of ordinary skills in the optical and instrument arts will recognize that an incident beam, from for example light source (300) or from scattered light will be communicated throughout the optical train.

FIG. 2a is a cross sectional plane that includes the sample chamber axis 210 and which illustrates the path of the transmitted UV light beam sequentially from the light source (300) to right angle prism or mirrors or dove prisms and to illuminate the at least one photodetector (400).

Figure 2G:
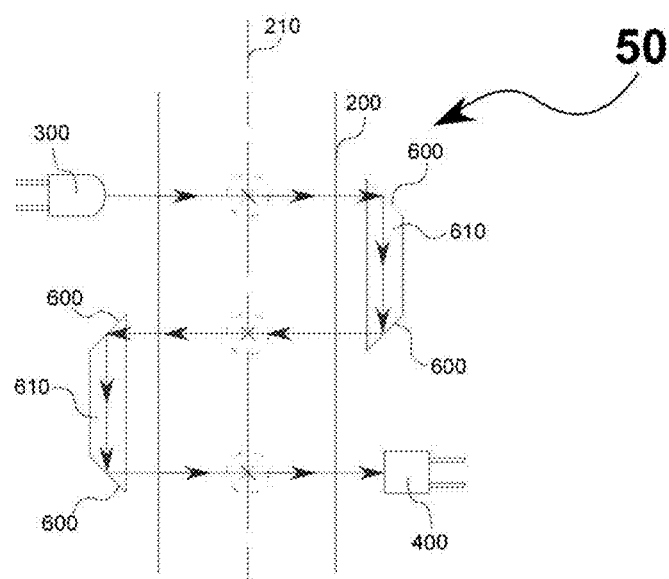
FIG. 2g is illustrative of "n" passes of light, seen here as 3 passes, through the sample. Shown is a sample vessel (200), sample chamber axis (210), one light source (300) and first photodetector (400).

FIG. 2 shows an embodiment similar to FIG. 2g, but illustrating additional reflective elements (600) and multiple photodetectors. For clarity, neither the sensor body (100) nor the sample vessel (200) are fully shown. FIG. 2 also depicts the instrument with two passes of the light beam through the sample instead of the three passes shown in FIG. 2g. Also illustrated are reflective elements (600) which are preferably right-angle prisms or dove prisms (610) that comprise two reflective elements but may be mirrors which re-direct transmitted and scattered light paths through the respective at least one first optical train (50), the at least one second light train (53) and the at least one third optical train (54). Persons of ordinary skill in optics will recognize from FIG. 2 how the prisms or other reflective elements must be aligned and fixed to direct the transmitted and scattered light beams as shown in the figure. Persons so skilled will also recognize that if prisms are used as the reflective elements (600), clearance between the rear of the angled reflecting facet and the sensor body reflective element space (700)

must be maintained to prevent optical contact between the facet and the sensor body and consequent light loss. In a preferred embodiment, reflective element space (700) is at least 0.25 mm.

It is also seen, in FIG. 2b, that the at least one second photodetectors (410) and the at least one third photodetectors (420) occupy the four positions representing termini of scattered light beams paths.

FIG. 2a is a cross sectional plane that includes sample chamber axis (210) and shows the path of the transmitted light source (300) UV light beam sequentially from light source (300) to reflective elements (600) and to photodetector (400).

It will be understood by persons of ordinary skill in optical and measurement instrument arts that redirecting light, whether from a light source such as at least one light source (300) or from scattered light, can be done with mirrors and prisms. In this disclosure redirection of light is indicated to be redirected "diametrically" which herein means that the light is generally redirected orthogonally and coincidentally with a diameter or cord of the sample chamber (110), through the sample chamber axis (210) and the sample vessel (200) and orthogonally and coincident to the sample chamber axis (210).

A person of ordinary skill in measuring instrument arts will recognize the following: 1. that the colorimeter body (100) will generally be made from a rigid material in order to retain alignment of the optical train such as Delrin®; 2. that the at least one light source (300), at least one photodetector (400), at least one reflective element (600) and, when there are more than at least one, that all are affixed to the body (100) so that they are immobile retaining their position in the optical train so that an incident beam or scattered light is communicated through the entirety of the optical train to make illumination contact with an at least one photodetector.

FIG. 2g illustrates reflecting elements (600) used to direct the light source (300) UV light beam three times through the sample instead of once, and the view shows the at least one second optical train (53) rotated by 90°. In FIG. 2g, the light path from the light source (300) is reflected two more times through the sample before it reaches the at least one photodetector (400) and hence the total Beer-Lambert path length is effectively tripled. The reflective elements (600), shown in FIG. 2g, are preferably established using dove prisms (610), each of which comprises two reflective elements and offsets and reverses the light beam by 180°.

FIG. 2g is illustrative of an embodiment of the invention where light from a light source (300) passes through an optical train (50), comprising light tunnel segments (500) and reflective elements (600), accomplishing three passes through a sample vessel (200) and into illumination contact with a photodetector (400).

FIG. 2c through FIG. 2f are cross sections further illustrating the arrangement of electro-optical and reflective components within sensor body (100).

To a person skilled in the art of colorimetric analysis, it is obvious that the reflective, optical, and electrical components within the sensor body (100) must be sealed against contact with fluid samples, and for an instrument intended for submerged deployment, the sensor body (100) must additionally include means to protect those same inner components from the external environment. It is further obvious that pump or flow processes or methods must be provided to move the fluid sample into and from the sample vessel (200) continuously or intermittently.

Figure 3:
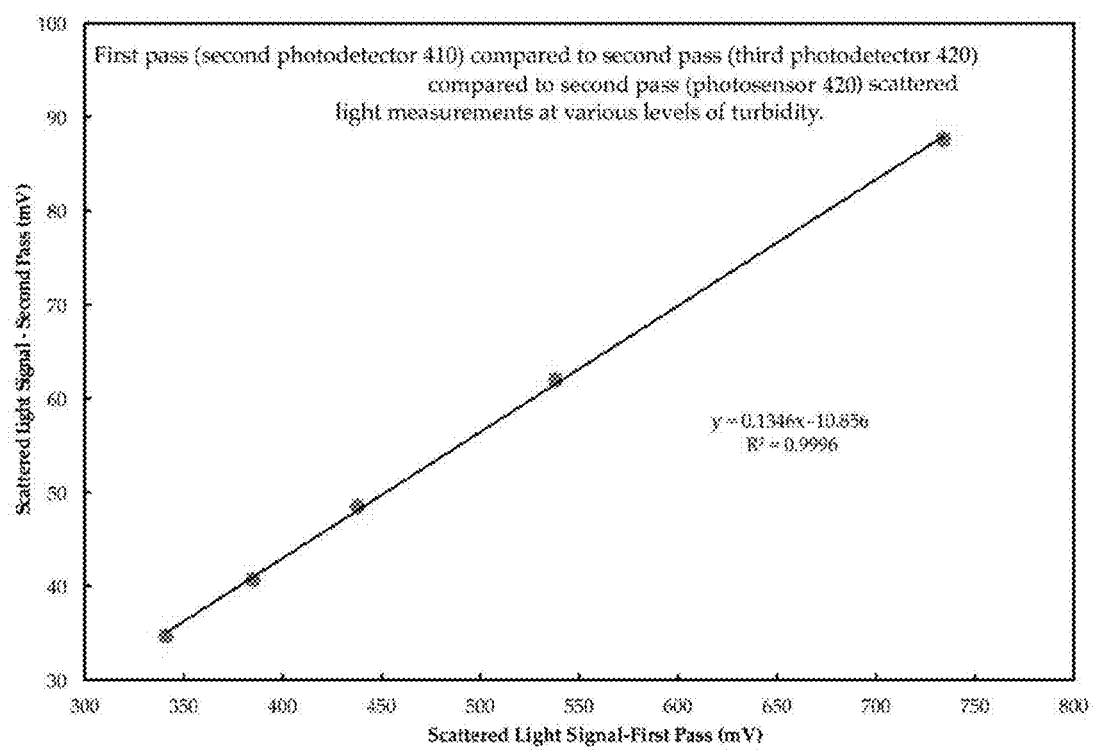
FIG. 3 is a graphic comparison of the intensity of scattered light simultaneously measured at second photodetectors (410) and third photodetectors (420) for five samples of water having different levels of turbidity. Seen is the scattered light intensity measured by third photodetectors (420) is approximately 13% of the light intensity measured the second photodetectors (410).

FIG. 3 is a graph that compares signal strength in millivolts at the at least one second photodetectors (410) and the at least one third photodetectors (420) measuring light scattered within the at least one third optical train (053) and the at least one third optical train (054), respectively, for various levels of turbidity causing up to 30% signal loss detected by the at least one photodetector (400).

An embodiment of the Apparatus for Measuring the Amount of a Chemical Within a Turbid Sample comprises a colorimeter (1) having a colorimeter body (100), the body (100) having a sample chamber (110); a sample vessel (200) is accommodated by the sample chamber (110); a sample is flowed through the sample vessel (200); and, at least one optical train (50), having at least one light tunnel segment (500); said at least one light tunnel segment (500) having reflective elements (600) positioned therein directing light through the at least one optical train (50) and through the sample vessel (200) at least once and into illumination contact with at least one photodetector (400); and, an output voltage from the said at least one photodetector (400) is a factor for determining concentration of a chemical in the sample.

In a preferred embodiment of the invention the body (100) has an outside (140), a top (180) and a bottom (190); and, the body (100) and the sample chamber (110) are generally cylindrical, having a sample chamber axis (120) centrally positioned within the sample chamber (110) from the said top (180) to the said bottom (190); and the said sample vessel (200) is generally cylindrical in shape, is transparent and is sized to be friction received into the said sample chamber (110); and at least one light source (300) is affixed to the body (100); an incident beam, from the said at least one light source (300) is directed into the said at least one optical train (50); the at least one photodetector (400) is affixed to the body (100), and is aligned with the said at least one optical train (50); the said at least one photodetector (400) is distal to the light source (300); and the at least one optical train (50) is comprised of at least one light tunnel segment (500) comprising a hole; and the said at least one light tunnel segment (500) extends downwardly from the said top (180) generally parallel with the said sample chamber axis (120) and intermediate the said outside (140) and the sample chamber (110); the at least one light source (300) is proximal the said top (180) directing an incident light beam into the said at least one optical train (50); the said at least one optical train (50) is further comprised of has at least one light tunnel increment (500) downwardly extending; the said at least one light tunnel increment (500) distal to the said at least one light source (300) turns diametrically, intermediate the said top (180) and the said bottom (190), and penetrating the said body (100) at the sample chamber (110) and continuing diametrically and penetrating the said sample chamber (110); and, intermediate the said sample chamber (110) and the said outside (140) the said at least one light tunnel segment (500) turns downwardly and the said at least one light tunnel segment (500) distal to the said sample chamber (110) and intermediate the said top (180) and the said bottom (190) turns diametrically penetrating the said body (100) at the sample chamber (110); and the said light tunnel segment (500) continuing and, intermediate the said sample chamber (110) and the said outside (140) the said at least one light tunnel segment (500) turns downwardly penetrating the said body (100) and exits the body (100) at the said bottom (190); and, the at least one photodetector (400) is proximal the said bottom (190) and is positioned in alignment with the said optical train (50) and is illuminated by the incident beam communicated by the said optical train (50) from the said light source (300); and, at each turn of the said at least one light tunnel segment (500) a reflective element (600) is immovably positioned re-directing the said incident light beam generally by 90 degrees; and, at least one second optical train (53) comprising at least one light tunnel segment (500) is formed, from at least one light tunnel segment (500) having reflective elements (600), to detect scattered light, proximal the said top (180), from within the sample vessel (200) having at least one second photodetector (410) positioned to detect scattered light; and, a signal from said at least one second photodetector (410) comprising an output signal from the said at least one second photodetector (410) which is a factor for determining the concentration of hexavalent chromium in the sample; and, at least one third optical train (54) comprising at least one light tunnel segment (500) is formed, from at least one light tunnel segment (500) having reflective elements (600), to detect scattered light, proximal the said bottom (190), from within the sample vessel (200), between the said top (180) and the said bottom (190) and proximal the said bottom (190) having at least one third photodetector (420) positioned to detect scattered light; and, a signal from said at least one third photodetector (420) comprising an output signal from the said at least one third photodetector (420) which is a factor for determining the concentration of hexavalent chromium in the sample.

Technical Specifications

Figure 4:
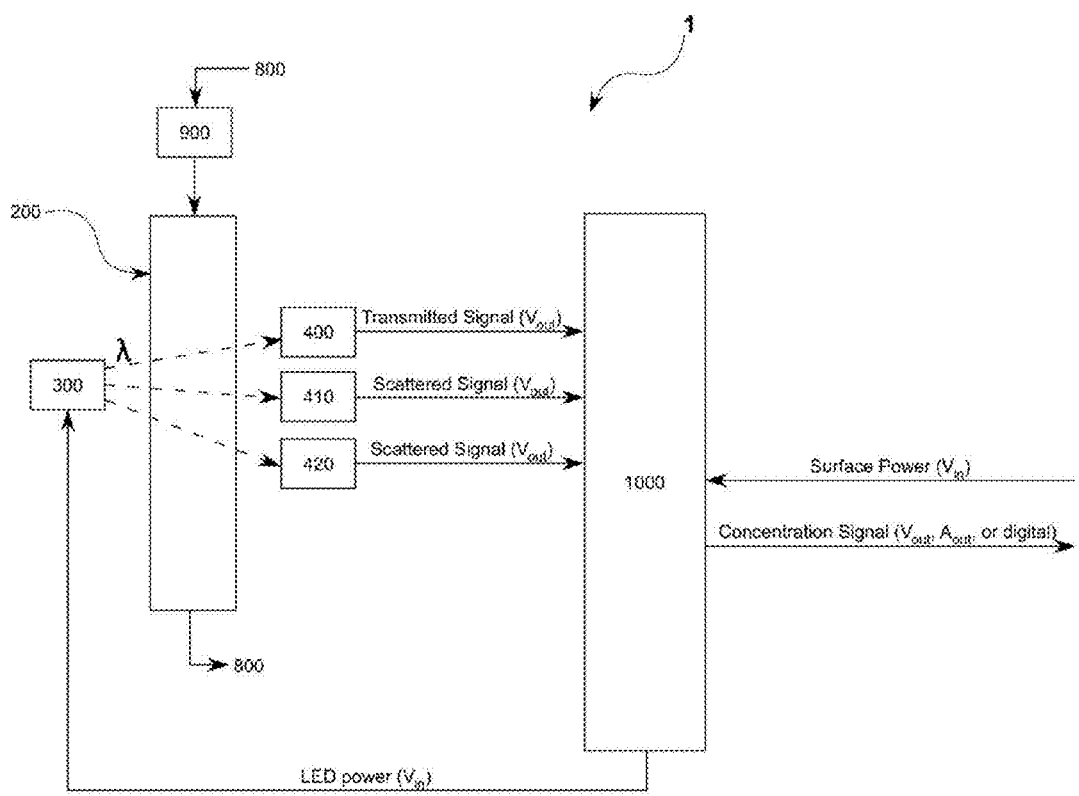
FIG. 4 is a block diagram showing the relationships of the electronic, optoelectronic, and mechanical components of a cable-deployed submersible preferred embodiment designed for environmental water quality monitoring. Electrical power via the cable energizes electronic circuit board (1000) which in turn energizes and controls a sample pump (900), a light source (300), and photodetectors (400, 410, and 420). The pump (900) moves water from the surrounding environment which becomes the sample (800) within the sample vessel (200). Within the sample vessel (200) the sample (800) is illuminated by the light source (300). Voltages representing transmitted and scattered light signals are sent to circuit board (1000) and further sent to the surface from the circuit board (1000) in the form of voltages, currents, or digital data.

A preferred embodiment as represented in FIG. 2a through 2f and in FIG. 4, having an outer diameter of 39 mm and a Beer-Lambert path length of 34 mm comprised the following components:

---

Sample vessel (200)

Friedrich and Dimmock
Heraus HSQ 300 Quartz, #HA-17201
17 mm ID × 20 mm OD fused quartz tubing
Pump (900)

Simply Pumps
HP Miniature Pump
HP100S
Reflecting element (600)

Thorlabs, Inc.
Right-Angle Prism, N-BK7 glass, uncoated, 5 mm
PS909
Dove prism (610)

Thorlabs, Inc.
N-BK7, uncoated, 5 mm
PS990
Light source (300)

Nichia Corporation
UV LED, 375 nm
NSPU510CS
Photodetector (400, 410, 420)

Radio Shack
NPN Silicon Phototransistor
276-0145

---

The invention claimed is:

1. An apparatus for measuring concentration of a chemical within a turbid sample, the apparatus comprising:
a colorimeter having a colorimeter body, the body having a sample chamber;
a sample vessel which is accommodated by the sample chamber and which is generally cylindrical in shape, transparent, and is sized to be friction received in the sample chamber;
at least one photodetector affixed to the body;
at least one optical train having at least one light tunnel segment, the at least one light tunnel segment is an aperture sized and shaped to receive reflective elements positioned therein to direct light through the at least one optical train and through the sample vessel at least once and into illumination contact with the at least one photodetector;
at least one light source which is affixed to the body, wherein an incident beam from the at least one light source is directed into the at least one optical train which is aligned with the at least one photodetector, the at least one photodetector distal to the at least one light source, wherein:
the body has an outside, a top, and a bottom;
the body and the sample chamber are generally cylindrical and having a sample chamber axis centrally positioned within the sample chamber from the top to the bottom; and
the at least one light tunnel segment extends downwardly from the top generally parallel with the said sample chamber axis and intermediate the outside and the sample chamber;
the at least one light source is positioned proximal to the top;
the at least one light tunnel segment extends downwardly distal to the at least one light source and turns diametrically, intermediate the top and the bottom, and penetrates the body at the sample chamber and continues diametrically and penetrates the sample chamber and, wherein:
intermediate the sample chamber and the outside, the at least one light tunnel segment turns downwardly, and
the at least one light tunnel segment distal to the sample chamber and intermediate the top and the bottom turns diametrically penetrating the body at the sample chamber,
the light tunnel segment continuing and, intermediate the sample chamber and the outside, the at least one light tunnel segment turns downwardly and penetrates the body and exits the body at the bottom, wherein the at least one photodetector is proximal the bottom and positioned in alignment with the optical train and is illuminated by the incident beam communicated by the optical train from the light source,
at each turn of the at least one light tunnel segment, the at least one light tunnel segment includes a reflective element from among the reflective elements, the reflective element immovably positioned to redirect the incident light beam generally by 90 degrees;
at least one second optical train including at least a second light tunnel segment and at least one second photodetector positioned proximal the top to detect scattered light from within the sample vessel, wherein:
the second light tunnel segment includes a second aperture extending downwardly from the top generally parallel with the sample chamber axis,
intermediate the outside and the sample chamber, the at least one second optical train is offset from the at least one optical train by about 1° to 90° degrees,
the at least one downwardly extending second light tunnel segment turns diametrically intermediate the top and the bottom and penetrates the body at the sample chamber and continues and, intermediate the sample chamber and the outside, the second light tunnel segment turns upwardly penetrating the body and exits the body at the top, at each turn of the second light tunnel segment, the second light tunnel segment includes a reflective element from among the reflective elements, and the at least one second photodetector is positioned at the top to receive illumination from the at least one second optical train;

at least one third optical train including at least one third light tunnel segment and at least one third photodetector positioned proximal the bottom to detect scattered light from within the sample vessel, wherein:

the third light tunnel segment includes a third aperture extending upwardly from the top generally parallel with the said sample chamber axis, intermediate the outside and the sample chamber, the at least one third optical train is offset from the at least one optical train by about 1° to 90° degrees, the at least one upwardly extending third light tunnel segment turns diametrically intermediate the top and the bottom and penetrates the body at the sample chamber and continues and, intermediate the sample chamber and the outside, the third light tunnel segment turns downwardly penetrating the body and exits the body at the bottom, at each turn of the third light tunnel segment, the third light tunnel segment includes a reflective element from among the reflective elements, and the at least one third photodetector is positioned at the bottom to receive illumination from the at least one third optical train; and wherein:

the at least one second optical train and the at least one third optical train are offset from the at least one optical train by 90°; and the at least one second photodetector and the at least one third photodetector are at least one of rigidly affixed to the body and removably affixed to the body; and the at least one second photodetector includes at least two second photodetectors where one of the two second photodetectors is positioned and directed into illumination contact with scattered light within the at least one second optical train at each point where the one second optical train enters or exits the top; and the at least one third photodetector includes at least two third photodetectors which are positioned and directed into illumination contact with scattered light within the at least one third optical train at each point where the one third optical train enters or exits the bottom; and the reflective element from among the reflective elements is immovably affixed at each turn of second light tunnel segment redirecting light 90 degrees; and the at least one second photodetector detects scattered light from the at least one second optical train at each penetration by the second light tunnel segment; and the at least one third photodetector detects scattered light from the at least one third optical train; and an output signal generated by each of the at least one photodetector, the at least second photodetector, and the at least third photodetector is a voltage from the at least one photodetector, the at least one second photodetector and the at least one third photodetector and is a factor for determining the concentration of hexavalent chromium in the sample.

2. A colorimeter for measuring a concentration of a chemical in a turbid sample, the colorimeter comprising:
a colorimeter body having a sample chamber;
a sample vessel to receive the turbid sample, the sample vessel disposed in the sample chamber;
a light source to emit an incident light beam;
a first photodetector configured to generate a first output signal corresponding to the concentration of the chemical in the turbid sample;
a plurality of first reflective elements disposed in the body which are arranged to direct the incident light beam through the turbid sample at least twice and to the first photodetector, the incident light beam travelling along orthogonal optical paths, the orthogonal optical paths including at least a first optical path from the light source to a first one of the reflective elements and a second optical path from the first one of the first reflective elements through the turbid sample to a second one of the first reflective elements, the first optical path being parallel to a sample chamber axis and perpendicular to the second optical path;
a second photodetector; and
a plurality of second reflective elements disposed in the body which are arranged to direct scattered light to the second photodetector.

3. The colorimeter of claim 2 wherein the first and the second photodetectors comprise photodiodes.

4. The colorimeter of claim 2 wherein the light source and the first photodetector are positioned at opposite ends of the body.

5. The colorimeter of claim 2 wherein at least the first one of the plurality of first reflective elements is arranged diametrically opposed to at least the second one of the plurality of first reflective elements across the sample chamber axis.

6. The colorimeter of claim 2, further comprising:
a third photodiode; and
a plurality of third reflective elements disposed in the body which are arranged to direct scattered light to the third photodetector.

7. The colorimeter of claim 6 wherein the second photodiode and the third photodiode are arranged at opposite ends of the body.

8. The colorimeter of claim 6 wherein the plurality of third reflective elements direct scattered light to the third photodiode in a first direction and the plurality of second reflective elements direct scattered light to the second photodiode in a second direction, the first direction being opposite to the second direction.

9. The colorimeter of claim 2 wherein the light source is positioned in a light tunnel segment, the light tunnel segment sized and shaped to at least partially collimate the incident light beam.

* * * * *